United States Patent [19]

Sutter et al.

[11] Patent Number: 5,230,625
[45] Date of Patent: Jul. 27, 1993

[54] VALVE ARRANGEMENT

[75] Inventors: Ralf Sutter, Mannheim; Lutz Beerstecher, Bensheim, both of Fed. Rep. of Germany

[73] Assignee: Siemens Aktiengesellschaft, Munich

[21] Appl. No.: 859,667

[22] Filed: Mar. 30, 1992

[30] Foreign Application Priority Data

Mar. 28, 1991 [EP] European Pat. Off. ........ 91105053.2

[51] Int. Cl.$^5$ .............................................. A61C 17/06
[52] U.S. Cl. ...................................... 433/95; 604/118
[58] Field of Search .................... 433/95; 604/33, 118, 604/119, 902; 137/628

[56] References Cited

U.S. PATENT DOCUMENTS

| | | | |
|---|---|---|---|
| 3,657,819 | 4/1972 | Soderqvist | 433/95 |
| 3,763,862 | 10/1973 | Spieth | 433/95 |
| 3,971,375 | 7/1976 | Hill | 604/118 |
| 4,274,411 | 6/1981 | Dotson, Jr. | 433/95 |
| 4,706,687 | 11/1987 | Rogers | 604/119 |
| 5,002,486 | 3/1991 | Cattani | 433/95 |

FOREIGN PATENT DOCUMENTS

| | | |
|---|---|---|
| 0355467-A1 | 2/1990 | European Pat. Off. . |
| 0355467-B1 | 12/1991 | European Pat. Off. . |
| 2037197 | 5/1972 | Fed. Rep. of Germany . |
| 2005567 | 2/1987 | Fed. Rep. of Germany . |
| 2035488 | 12/1970 | France . |

Primary Examiner—John J. Wilson
Attorney, Agent, or Firm—Hill, Steadman & Simpson

[57] ABSTRACT

A valve arrangement for controlling a suction stream in a dental suction system, wherein the valve controlling the flow contains a closure element that defines a valve space on one side and a control space on the opposite side. The closure element, such as a membrane, is urged closed when the pressure in the control space is greater than the pressure in the valve space and the movement of the closure element is obtained by actuation of various control valves which control flow in effective lines extending to the control space, which lines have different effective cross sections so as to control the amount of movement of the closure element toward the closed position.

10 Claims, 4 Drawing Sheets

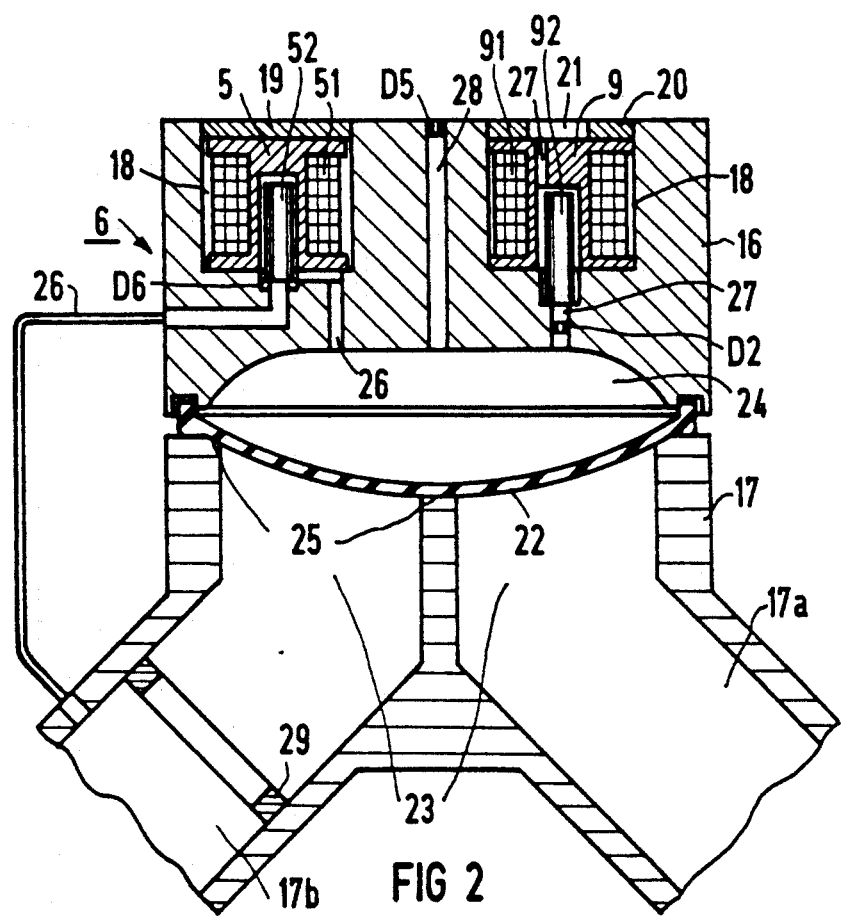
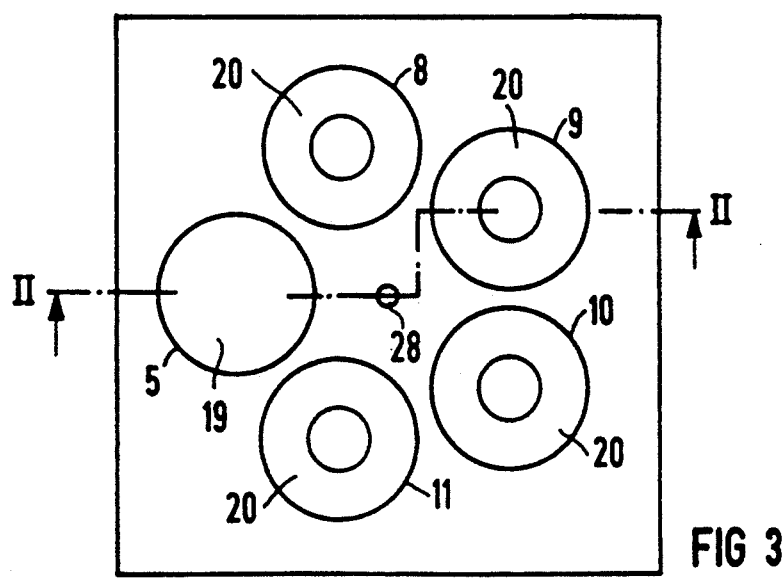

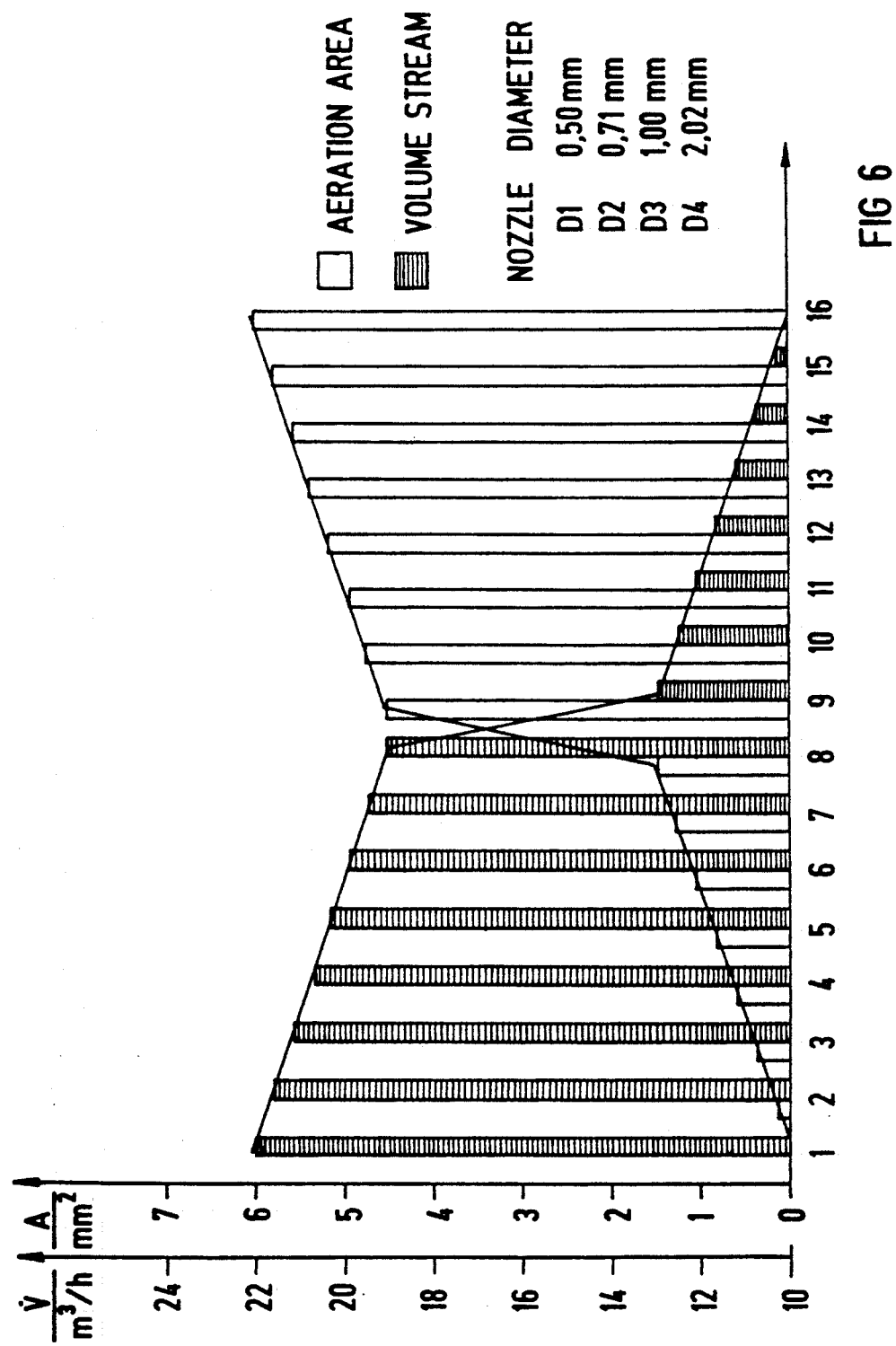

VALVE ARRANGEMENT

BACKGROUND OF THE INVENTION

The present invention is directed to a valve arrangement for controlling the flow of an airstream in an air flow system, preferably a suction stream in a dental suction system, wherein the valve arrangement contains a closure element or valve member that creates a valve space on one side and a control space on the other side so that pressure changes in the control space will change the position of the valve member to regulate the size of the valve space and, thus, regulate the flow therethrough.

The above valve arrangements are utilized in apparatus of dental medicine for controlling the suction airstream in a suction system for suctioning water, blood, saliva, tooth material, etc., from the oral cavity of a patient. U.S. Pat. No. 3,763,862, whose disclosure is incorporated herein by reference thereto and which claims priority from German Patent Application P 20 05 567.8, discloses a valve that defines the flow of an airstream and is arranged in the suction or vacuum line of an under-pressure or vacuum generator. As a closure element, the valve contains a membrane that divides the valve housing into an upper control space that is covered by a cover and into a lower space, which is the actual valve space that contains an inlet and outlet channel for the medium. The control space is in communication with the outlet channel via a connecting line. An aeration valve is connected into the connecting line, and this aeration valve connects the control space to the atmosphere when activated. The flow cross section in the valve space can be entirely opened or closed or can only be partially opened with the assistance of this aeration valve acting as a control valve.

Alternate to the above-mentioned aeration valve, the valve arrangement is also disclosed in this prior art wherein a line branches off from the connecting line between the valve space and the control space, with a free end of the line being constantly connected per se to the atmosphere and being capable of being closed by the operator for control as needed. In order to achieve a metering of the suction stream, it is proposed that a choke that is correspondingly actuated by the operator be integrated into this control line. The pressure difference at both sides of the membrane can be influenced with this choke and, thus, the flow of the medium can be controlled.

Another, similarly constructed valve arrangement is disclosed in German Application 38 27 176, which was the basis for European Application 0 355 467. In this reference, the upper control space of the valve is intermittently connected to the atmosphere either by an electromagnetically actuatable pre-control valve or an aeration valve that directly influences the membrane, which is switched on and off with a variable clock frequency. Such an intermittent drive necessarily leads to a high mechanical stress of the control elements.

SUMMARY OF THE INVENTION

An object of the present invention is to provide a valve arrangement which makes it possible to be able to set the airstream, particularly the suction stream and the strength of suction with different graduations, namely in a graduation which is selected by the user. A further object is to be able to set a plurality of levels for the suction strength with optimally few electrical signals.

To accomplish these goals, the present invention is directed to an improvement in a valve arrangement for controlling the flow of an airstream, such as a suction stream for dental suction systems, said valve arrangement including flow valve means for defining the flow which includes a closure element that separates a valve space from a control space with the valve space being connected to an inlet line and an outlet line and the control space containing pressure which will shift the valve closure element to change the size of the control space to control the amount of flow therethrough. The improvements are that the control space includes a plurality of control valves for controlling the flow of air having a higher pressure than in the valve space into the control space, a valve space being supplied via these control valves to the control space, wherein the effective line cross section for the higher pressure being supplied to the control space are dimensioned so that every control valve itself only effects a partial closing of the closure element and that the control valves can be optionally activated individually, collectively or, in groups in selected combinations.

This makes it possible to set the airstream, such as the suction stream, at a strength with different graduations, namely in a graduation selectable by the user. Thus, a possibility is created wherein the conversion of the control signal for achieving the desired graduation can be realized more easily with respect to the electrical drive and with lower wear.

A critical advantage of the invention can be seen wherein the setting of the strength of the suction can be individually adapted to the respective requirements. By selecting the cross sections with which the pressure elevation is achieved in the control space, it is, thus, possible to provide different valve characteristics. The number of possible settings of the strength of the suction is thereby dependent on the number of control valves that are provided. Thus, from the following description of the exemplary embodiment, sixteen possible settings for the strength of the suction already occur given four control valves.

Other advantages and features of the invention will be readily apparent from the following description of the preferred embodiments, the drawings and claims.

BRIEF DESCRIPTION OF THE DRAWINGS

FIG. 2 is a cross sectional view taken along the lines II—II of FIG. 3 of the valve arrangement in accordance with the present invention;

FIG. 3 is a plan view of the valve arrangement of FIG. 2;

FIG. 6 is a further valve characteristic showing the volume stream as a function of the setting of the strength of the suction.

DESCRIPTION OF THE PREFERRED EMBODIMENTS

Figure 1:
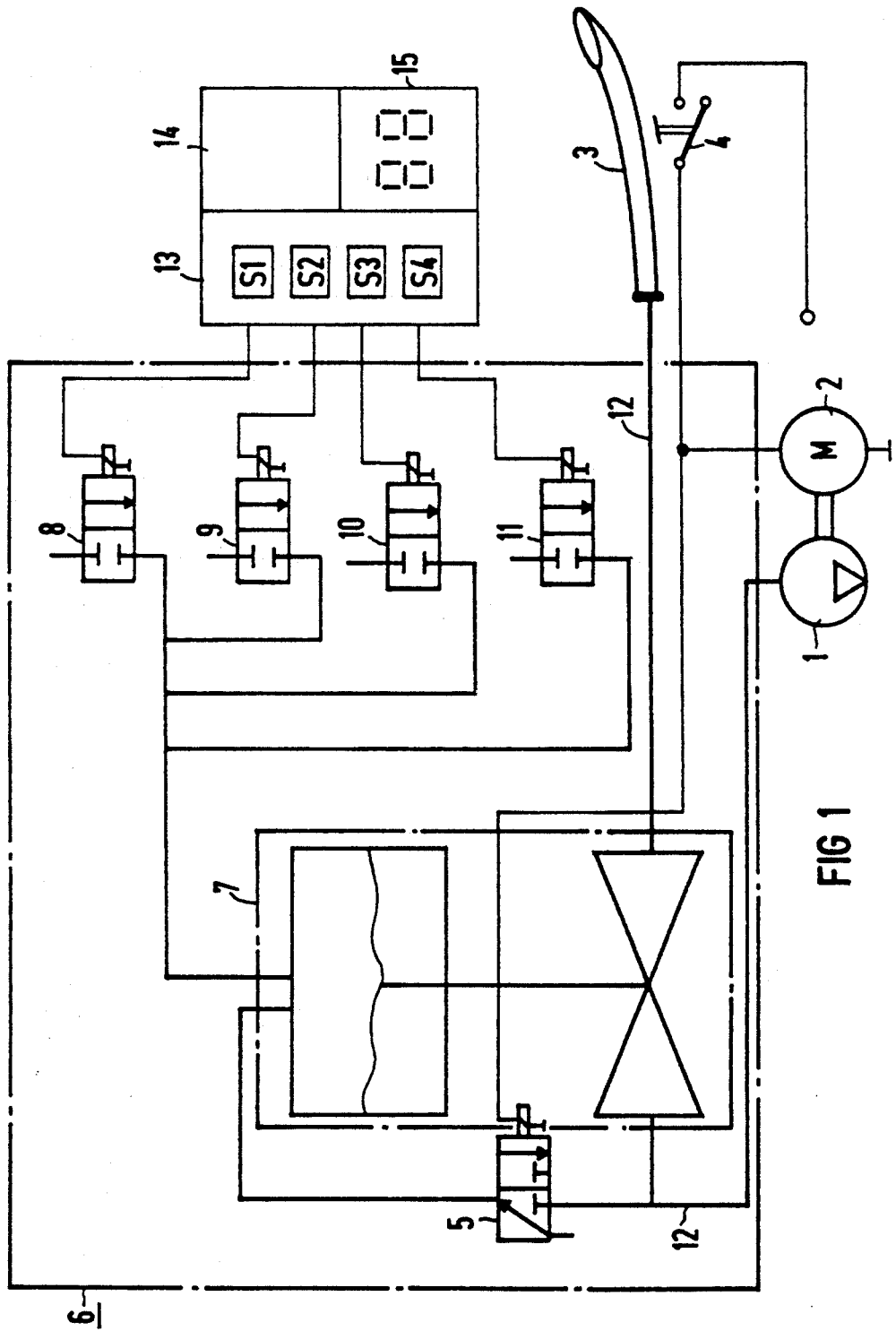
FIG. 1 is an electro-pneumatic circuit diagram for a dental suction system in combination with the valve arrangement according to the present invention.

The principles of the present invention are particularly useful when incorporated in an electro-pneumatic circuit diagram for controlling a dental suction system, as illustrated in FIG. 1. In this electro-pneumatic circuit diagram, a suction or vacuum generator 1 is driven by an electric motor 2 to create a suction stream suitable for extracting secretions and the like at a handpiece 3 in a known manner. The suction or vacuum generator 1 and the electric motor 2 can be separately switched on and off by a switch 4 that will respond to removal of the suction handpiece from a deposit or storage device. An electromagnetic on-off valve 5, which is part of a valve arrangement referenced 6, is switched with the actuation of the switch 4. In addition to the above-mentioned on-off valve 5, the valve arrangement 6 includes a valve 7 that controls the flow of airstream between the underpressure generator or vacuum source 1 and a suction handpiece 3 and also contains four control valves 8–11. The valve 7 controlling the flow of the medium that is shown in greater detail in a longitudinal section in FIG. 2 is connected into the suction line 12 between the suction handpiece 3 and the generator 1. Additional measures for separating the extracted particles, as well as the liquid that are usually provided in the suction line 12, are not shown in the circuit diagram, since they are not critical to the present invention.

The four control valves 8–11 are controlled from a control panel 13 that is arranged externally relative to the valve arrangement. To this end, the control panel 35 contains four switches S1–S4 allocated to the valves 8–11. In addition to the switches in the panel 13, an overview display regarding the various switching possibilities of the valves, as well as a display 15 at which a preselectable strength of the suction can be digitally displayed in a percentage, are provided.

As best illustrated in FIG. 2, the valve 6 has two valve housing halves 16 and 17 which form a compact valve unit when in their assembled condition. The lower valve half 17 contains connecting branches 17a and 17b that are connected to the suction line 12 in a suitable manner. As illustrated in FIG. 3, the on-off valve 5, as well as the four control valves 8–11, are arranged in a star-shaped pattern around a center in the upper housing half 16. To this end, the housing 16 has corresponding depressions or cavities for the acceptance of the valves, as well as corresponding covers 19 and 20. The cover 19 for the valve 5 is closed and, thus, tightly closes off the valve from the atmosphere; however, the covers 20 for the valves 8–11 are provided with an aeration bore 21.

The valve 17 that determines the flow of the medium contains a membrane 22 as a closure element that will limit a valve space 23 between an inlet branch 17b and outlet branch 17a, on the one hand, and also defines a control space 24, on the other hand. The flow valve 17 is shown here in a closed position, wherein the membrane 21 lies on the valve seat 25 and, thus, closes the valve space 23 between the inlet and outlet.

The membrane 22 is switched by pressure changes in the control space 24. Switching on and off occurs via the on-off valve 5 that, in the activated condition, produces a connection via a branch 26 of the line section of the suction line 12 situated between the generator 1 and valve 7. As already mentioned, the on-off valve is switched dependent on the removal of the suction handpiece 3 so that the valve 5 is actuated when the suction handpiece is picked up from its storage device and a coil 51, which is part of the valve, will have current flowing through it. A valve plunger 52 is lifted off of the valve seat when current flows through the coil 51 and, therefore, will connect the suction line 12 through the line 26 to the control space 24. As a result of the suction that is applied to the control space 24, the membranes 22, which is shown in a closed position, will be lifted off of the valve seat 25 to connect the inlet 17b to the outlet 17a.

In order to achieve an increasing pressure in the control space 24 and to, thus, bring the membrane 22 from the completely opened position into or toward a closed position, the control valves 8–11 are provided with aeration channels 27, which extend between an aeration bore 21 in the cover 20 and the space 24. When a valve, such as 9, is activated, a core 91 has electrical current passing therethrough to raise a plunger 92 from a seat to open the channel 27. With deactification, the plunger 92 will close the channel 27 to prevent further flow therethrough. In addition to the aeration channels controlled by the valves 8–11, another aeration channel 28, that constantly connects the control space 24 to the atmosphere via an aeration bore, is provided in the center of the housing 16.

The effective cross section of the aeration channels 27 of each of the control valves 8–11, of the on-off valve 5, as well as the aeration channel 28, are defined by nozzles D1–D6, which are arranged in each of these channels. The nozzles D1–D4 are allocated to the control valves 8–11. In combination with the nozzle D6, which is in the on-off valve 5, the cross section of the nozzles D1–D5 will define the degree of pressure elevation and, thus, the position of the membrane 22 as a result whereof the flow and, thus, the strength of the suction can be individually set. The effective aeration cross section of the nozzles D1–D5 of the control valves 8–11 can be graduated according to various criteria. Thus, the nozzles D1–D4 for the valves 8–11 can be formed by bores, whose diameters are linearly or quadratically graduated. It is, likewise, conceivable to correspondingly graduate the cross sectional areas of the nozzles D1–D4.

Figure 4:
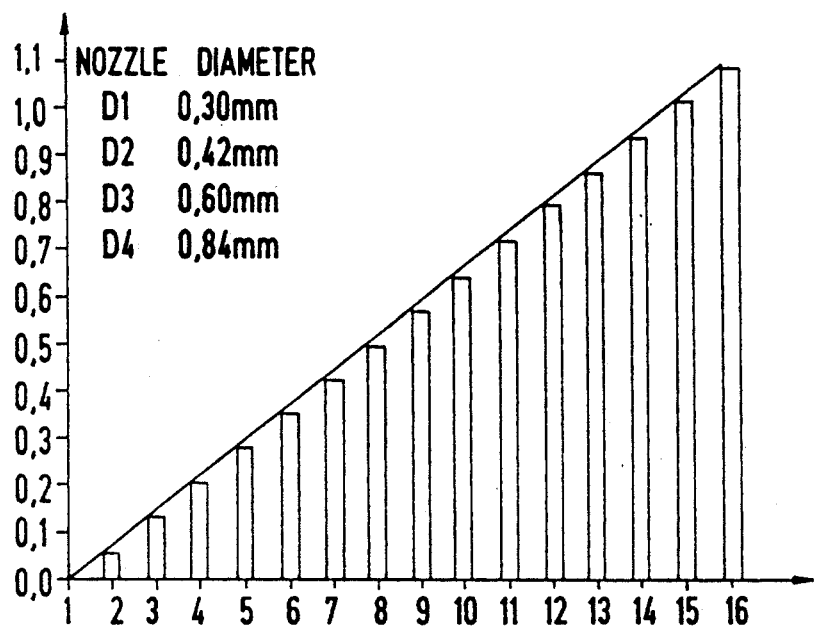
FIG. 4 is a graphic presentation of the first valve characteristic having a quadratic nozzle surface design given four control valves, with the abscissa showing the sixteen possible combinations of openings for the four control valves.
Figure 5:
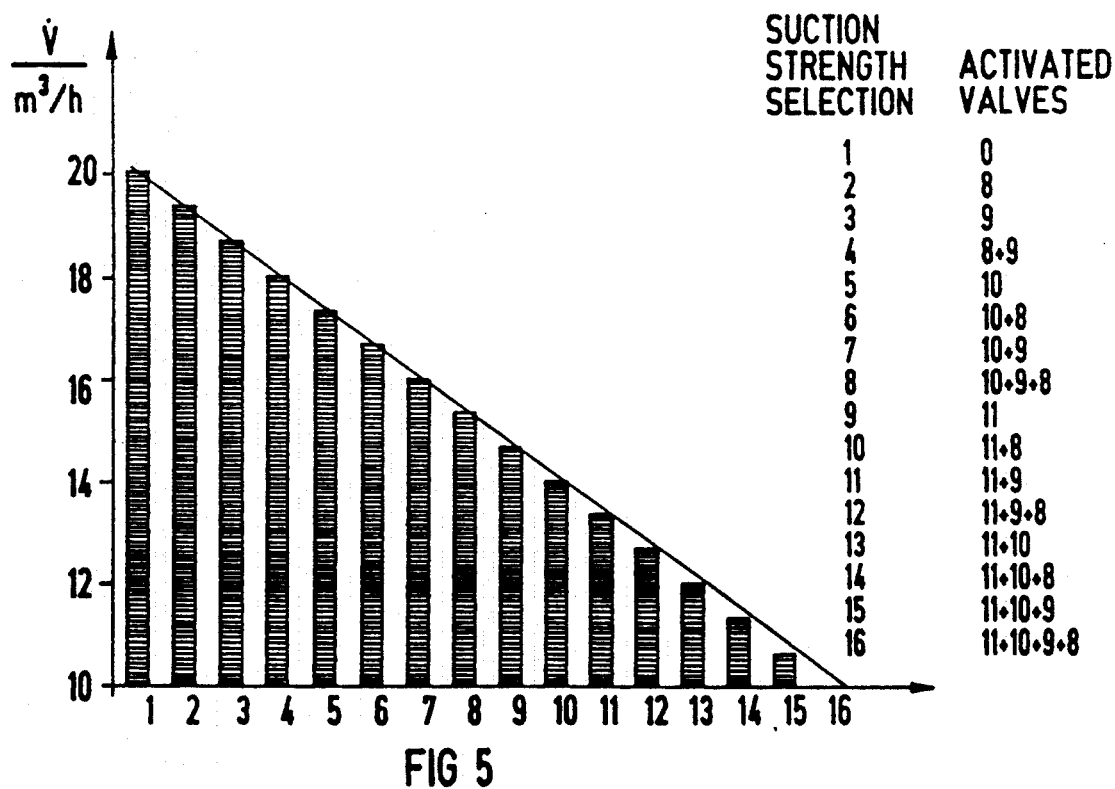
FIG. 5 is a graphic illustration of the control of the flow quantity dependent on the setting of the strength of the suction given a design of the control on the setting of the strength of the suction given a design of the control valve according to FIG. 4.

Various valve characteristics and effects that are obtainable are graphically shown in FIGS. 4–6. FIG. 4 shows a first valve characteristic that shows the nozzle are effective for the control as a function of the setting of the strength of the suction, namely given a quadratic design of the nozzle area for the four nozzles D1–D4, whereby the allocation of the diameter of each of these nozzles is indicated in the drawing. The graphics in FIG. 5 show the volume stream to be set given a nozzle area design of FIG. 4 as a function of the setting of the strength of the suction, whereby the allocation of the individual level of strength of the suction to the actively engaged valves is also shown, in addition to the graphic illustration. Corresponding to the $2^n$ switching possibilities that exist given n control valves, sixteen levels of setting for the strength of the suction are possible in the present application. As may be seen from the graphics, a practically linear valve characteristic and, thus, approximately linear graduation of the volume stream occurs for the sixteen possible settings of the strength of suction. The strength of the suction can, thus, be set in sixteen steps from a maximum to a minimum flow quantity, potentially down to zero. Dependent on which of the four control valves is activated, the aeration area of greater or lesser size occurs as a result whereof a corresponding increase in the pressure is established in the control space. The membrane 22 will thereby open to such an extent until an equilibrium of forces between the control space and the valve space has been established.

FIG. 6 shows a valve characteristic having a quadratic design of the valve area for the nozzles D1–D3 and having a second operating point on the basis of the nozzle D4, whereby the effective aeration area (A/mm$^2$), on the one hand, and the volume stream (V/m$^3$/h) which are established in the flow valve are shown in the graphics as a function of the setting of the strength of suction. It may be seen from the graphics that a steep rise in the engagement of the effective aeration area is established in the middle range of adjustments between levels 8 and 9, since the nozzle D4, which has a significantly larger opening cross section than the nozzles D1–D3, whose effective cross sectional areas are quadratically graduated, is activated here for the first time. A relatively pronounced pressure elevation is, thus, established in the control space, and this leads thereto that the membrane 22 is displaced to a corresponding extent in the direction of the closed position. The volume stream in the flow valve can, thus, be intentionally greatly reduced beginning with level 9. This is advantageously desired, for example, in order to be able to spontaneously switch from a high suction power, for example with suction handpieces, to a low suction, for example with a saliva extractor.

The slopes of the valve characteristics can be influenced by varying the effective cross section of the nozzle D6 of the on-off valve 5, as a result whereof the initial volume stream can be matched to the requirements when the control valves are not activated (position 1 for the strength of suction).

Instead of the forced aeration via the aeration channel 28, an aeration can also be provided in the on-off valve in that the valve seat of this valve is designed so that the plunger that opens a first valve seat (the opening of the nozzle D6 in FIG. 2) closes a second valve seat in its opened condition and vice versa, the second valve seat having a connection to the atmosphere. This design has the advantage that no flow losses occur and that a throttle location or restrictor 29 provided for compensating the pressure loss in the connecting branch 17b can be removed.

Although the design of the valve arrangement of the invention that has been set forth is especially advantageous, particularly allowing an extremely compact structure, other designs are possible within the framework of the invention. For example, a tappet valve member can also be provided instead of the membrane. This tappet valve is controlled via corresponding pneumatic and/or, in the present case, electromagnetic valves. The provision of the mechanically controlled valves is also fundamentally possible.

Instead of operating with the four switches S1–S4, the drive of the four control valves 8–11 can also occur with a single plus/minus switch in combination with a corresponding control electronics, wherein the individual setting of the strength of the suction which is to be selected can then be advantageously displayed at the display 15 in percentages of the maximum volume stream.

Although various minor modifications may be suggested by those versed in the art, it should be understood that we wish to embody within the scope of the patent granted hereon all such modifications as reasonably and properly come within the scope of our contribution to the art.

We claim:

1. In a valve arrangement for controlling the flow of an airstream in an air flow system, preferably for controlling the suction stream in a dental suction system, said valve arrangement comprising a flow valve means including a closure element that defines a valve space on one side and a control space on the opposite side, with changes of pressure in the control space moving the closure element and a higher pressure in the control space than in the valve space causing the closure element to move toward a closed position, the improvements comprising changes in pressure in the control space being obtained by a plurality of control valves, each control valve controlling the flow of air at a higher pressure than in the valve space into the control space, the effective line cross section of each of the control valves being dimensioned so that every control valve itself only effects a partial closing of the closure element and that the control valves can be optionally activated individually, collectively or in selected groups.

2. In a valve arrangement according to claim 1, wherein effective line cross sections allocated to the control valves are of a different size.

3. In a valve arrangement according to claim 2, wherein the line cross sections are formed by opening whose areas are quadratically graduated.

4. In a valve arrangement according to claim 2, wherein the line cross sections of all of the control valves except one are quadratically graduated and said one control valve comprises a significantly larger cross section in comparison to the other cross sections so that its actuation causes a second operating point to be formed.

5. In a valve arrangement according to claim 1, wherein an on-off valve is provided for achieving a pressure compensation between the valve space and the control space, said on-off valve, when activated, connecting the control space to the valve space via a branch line.

6. In a valve arrangement according to claim 5, wherein the control valves and the on-off valves are arranged in a housing section of the flow valve.

7. In a valve arrangement according to claim 6, wherein the on-off valve and control valves are arranged star-like around a center point in depressions formed in the housing section.

8. In a valve arrangement according to claim 7, wherein the control valves and on-off valves are electromagnetic valves that are activated via a control panel arranged externally with respect to the flow valve.

9. In a valve arrangement according to claim 8, wherein each of the electromagnetic valves is a solenoid valve having a plunger arranged in a coil member, said plunger closing a delivery channel when the flow valve means is opened and leaving the delivery channel open when the flow valve means is closed.

10. In a valve arrangement according to claim 1, wherein the flow through the air flow system is at a pressure less than atmospheric pressure and said flow valve means includes an aeration channel constantly in communication with the control space, said aeration channel being provided with an effective cross section dimensioned so that the pressure compensation that can be achieved via said aeration channel will not lead to any noteworthy closing of the closure element when the control valves are not actuated.

* * * * *